United States Patent
Farran et al.

(10) Patent No.: US 10,543,161 B1
(45) Date of Patent: *Jan. 28, 2020

(54) METHODS FOR PROTECTING AND IMPROVING THE APPEARANCE OF SKIN

(71) Applicant: L'OREAL, Paris (FR)

(72) Inventors: Alexandra Jane Elisa Farran, Dayton, NJ (US); Anne-Laure Suzanne Bernard, New-York, NY (US); Erin McMullin, Ewing, NJ (US); Brian Scott Bodnar, Manasquan, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/111,415

(22) Filed: Aug. 24, 2018

(51) Int. Cl.
| | |
|---|---|
| *A61K 8/81* | (2006.01) |
| *A61Q 19/00* | (2006.01) |
| *A61K 8/87* | (2006.01) |
| *A61K 8/25* | (2006.01) |
| *A61K 8/893* | (2006.01) |
| *A61K 8/02* | (2006.01) |
| *A61Q 19/08* | (2006.01) |
| *A61Q 19/02* | (2006.01) |
| *A61K 8/06* | (2006.01) |
| *A61K 8/35* | (2006.01) |
| *A61K 8/37* | (2006.01) |
| *A61K 8/40* | (2006.01) |
| *A61Q 17/04* | (2006.01) |

(52) U.S. Cl.
CPC .......... *A61K 8/8147* (2013.01); *A61K 8/0245* (2013.01); *A61K 8/062* (2013.01); *A61K 8/064* (2013.01); *A61K 8/25* (2013.01); *A61K 8/35* (2013.01); *A61K 8/37* (2013.01); *A61K 8/40* (2013.01); *A61K 8/8152* (2013.01); *A61K 8/8158* (2013.01); *A61K 8/87* (2013.01); *A61K 8/893* (2013.01); *A61Q 17/04* (2013.01); *A61Q 19/00* (2013.01); *A61Q 19/02* (2013.01); *A61Q 19/08* (2013.01); *A61K 2800/48* (2013.01); *A61K 2800/592* (2013.01); *A61K 2800/594* (2013.01); *A61K 2800/623* (2013.01); *A61K 2800/624* (2013.01); *A61K 2800/651* (2013.01); *A61K 2800/884* (2013.01); *A61K 2800/95* (2013.01)

(58) Field of Classification Search
CPC ...... A61K 8/8147; A61K 8/87; A61K 8/8152; A61K 8/25; A61K 8/893; A61K 8/0245; A61K 8/8158; A61K 8/062; A61K 8/064; A61K 8/35; A61K 8/37; A61K 8/40; A61K 2800/48; A61K 2800/884; A61K 2800/594; A61K 2800/624; A61K 2800/623; A61K 2800/651; A61K 2800/592; A61K 2800/95; A61Q 19/00; A61Q 19/08; A61Q 19/02; A61Q 17/04
See application file for complete search history.

(56) References Cited

U.S. PATENT DOCUMENTS

| | | | |
|---|---|---|---|
| 5,728,028 A | 3/1998 | Dusch | |
| 7,850,954 B2 | 12/2010 | Leblanc et al. | |
| 8,691,202 B2 | 4/2014 | Yu et al. | |
| 8,790,669 B2 | 7/2014 | Li et al. | |
| 9,017,704 B2* | 4/2015 | Blin ........................ | A61K 8/26 424/401 |
| 9,713,587 B2 | 7/2017 | Nijakowski | |
| 2007/0140991 A1 | 6/2007 | Maitra et al. | |
| 2007/0224140 A1 | 9/2007 | Quadir et al. | |
| 2010/0003004 A1 | 1/2010 | Hikita et al. | |
| 2012/0308496 A1 | 12/2012 | Viala et al. | |
| 2015/0342845 A1* | 12/2015 | Hwang ..................... | A61K 8/25 424/60 |
| 2017/0035680 A1 | 2/2017 | Gosto et al. | |
| 2017/0189320 A1 | 7/2017 | Chiou et al. | |

FOREIGN PATENT DOCUMENTS

| | | | |
|---|---|---|---|
| EP | 1513491 | * | 2/2009 |
| FR | 2924022 A1 | | 5/2009 |
| FR | 2925319 A1 | | 6/2009 |
| FR | 2983723 A1 | | 6/2013 |
| WO | 03086342 A1 | | 10/2003 |
| WO | 2007078486 A2 | | 7/2007 |
| WO | 2008115695 A1 | | 9/2008 |
| WO | PCT/US2011/050003 | | 3/2012 |
| WO | WO-2013/088051 A2 | | 6/2013 |
| WO | WO-2017/117426 A1 | | 7/2017 |

OTHER PUBLICATIONS

Weiner (2017).*
Dragoumis (2016).*
Wikipedia (2016).*
International Search Report and Written Opinion dated Nov. 5, 2019 for corresponding PCT Application No. PCT/US2019/047372.

* cited by examiner

Primary Examiner — Shirley V Gembeh
(74) Attorney, Agent, or Firm — Polsinelli PC

(57) ABSTRACT

The present disclosure relates to methods for protecting skin from UV radiation while simultaneously improving the appearance of skin. The methods include layered application of a skin perfecting composition and a sunscreen composition. The skin perfecting composition comprises: (i) about 1 to about 40 wt. % of at least one primary film forming polymer having a Young's modulus of 0.1 to 50 MPa, and elongation at break >50% and a glass transition temperature of <0° C.; (ii) about 1 to about 35 wt. % of at least one pressure sensitive adhesive polymer; (iii) about 1 to about 35 wt. % of soft focus powder; and (iv) water. The sunscreen composition comprises: (i) at least one organic UV filter; and (ii) a cosmetically acceptable carrier.

23 Claims, No Drawings

METHODS FOR PROTECTING AND IMPROVING THE APPEARANCE OF SKIN

FIELD OF THE DISCLOSURE

The present disclosure relates to methods for boosting SPF and UVA-PF while simultaneously improving the appearance of skin.

BACKGROUND

Most individuals are exposed to large amounts of ultraviolet (UV) radiation throughout their lifetimes due primarily to sunlight exposure. Sunlight includes two types of UV rays: long wave ultraviolet A (UVA) and short wave ultraviolet B (UVB), both of which can damage skin. UVA rays account for up to 95 percent of the UV radiation reaching the Earth's surface. Although they are less intense than UVB rays, UVA rays are 30 to 50 times more prevalent. They are present with relatively equal intensity during all daylight hours throughout the year, and can penetrate clouds and glass.

UVA rays penetrate the skin more deeply than UVB rays and have long been known to play a major part in skin aging and wrinkling (photo-aging), but until recently scientists believed that UVA rays did not cause significant damage to the epidermis (outermost skin layer) where most skin cancers occur. Studies over the past two decades, however, show that UVA radiation damages skin cells called keratinocytes in the basal layer of the epidermis.

Both UVA and UVB radiation contribute to skin damage that accelerates the appearance of aging, for example, loss of skin elasticity and the appearance of wrinkles. This process is commonly referred to as photo-aging. As skin ages, the outer skin layer (epidermis) thins, even though the number of cells remain largely unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity, which becomes more noticeable in sun-exposed areas (solar elastosis). Elastosis produces the leathery, weather-beaten appearance common to farmers, sailors, and others who spend a large amount of time outdoors.

SUMMARY OF THE DISCLOSURE

The methods of the current invention provide a surprising improvement in sun protection factor ("SPF") and ultraviolet-A protection factor ("UVA-PF") while simultaneously improving the appearance of skin. The methods include layering onto skin a skin perfecting composition and a sunscreen composition. The surprising improvement in SPF and UVA-PF occurs regardless of the order of application, i.e., the skin perfecting composition can be applied first followed by application of the sunscreen compositions or vice versa.

In addition to boosting the SPF and UVA-PF, which provides full spectrum photo-protection to the skin, the methods provide and an immediate and dramatic improvement to the appearance of skin, for example, by reducing the appearance of wrinkles, eye bags, pores, and skin imperfections such as scarring, dark spots (and uneven skin tone), dark circles, and roughness. This results from application of the skin perfecting compositions, which includes film-forming polymers, pressure sensitive adhesive polymers, and soft focus powder. Unlike other products, the films formed on the skin do not dry-out, whiten, crack, or peel. Instead, they remain flexible (elastic), durable, and comfortable. Moreover, the compositions (and resulting films) hydrate and protect the underlying skin.

The skin perfecting compositions typically include:
(i) at least one primary film forming polymer having a Young's modulus of 0.1 to 50 MPa, and elongation at break >50% and a glass transition temperature of <0° C.;
(ii) at least one pressure sensitive adhesive polymer;
(iii) soft focus powder; and
(iv) water.

Said primary film forming polymer may be a polyurethane latex polymer, for example, those that are formed by reacting a di- or polyisocyanate with a diol and/or polyol, including for example, aqueous polyurethane dispersions. Non-limiting examples include polyurethane 32, polyurethane-34, polyurethane-35, polyurethane-48, and a mixture thereof. In some cases, the cosmetic compositions preferably include at least two primary film forming polymers having a Young's modulus of 0.1 to 50 MPa, and elongation at break >50% and a glass transition temperature of <0° C., for example, polyurethane-34 and polyurethane-35.

Non-limiting examples of pressure sensitive adhesive polymers include copolymers of acrylate and methacrylate, rubber-based polymers, and styrene copolymers (such as styrene-isoprene-styrene (SIS) and styrene-butadiene-styrene (SBS) copolymers). In some instances, the pressure sensitive adhesive polymer is an acrylate polymer, for example, a copolymer of butyl acrylate, butyl methacrylate or acrylic acid. A non-limiting examples of such polymer is 2-ethylhexylacrylate (also referred to as (poly)ethylhexylacrylate).

Soft focus powders are useful for providing blurring effects, which provides skin with a smoother appearance, for example, by reducing the difference in luminosity between the valley and the edges of wrinkles and imperfections. For example, soft focus powders may be powders of natural or synthetic origin such as mica, titanated mica, alumina, aluminum silicate, silica which may or may not be coated, fumed silica, silica silylate, titanium dioxide, serecite, composite talc/titanium dioxide/alumina/silica powders, polyamide, poly(methyl (meth)acrylate), polyethylene powder, polymethylsilsesquioxane powder, and a mixture thereof.

The sunscreen compositions typically include:
(i) at least one organic UV filter; and
(ii) a cosmetically acceptable carrier.

Non-limiting examples of organic UV filters include para-aminobenzoate derivative, a salicylate derivative, a cinnamate derivative, a benzophenone or an aminobenzophenone derivative, an anthranillate derivative, a β,β-diphenylacrylate derivative, a benzylidenecamphor derivative, a phenylbenzimidazole derivative, a benzotriazole derivative, a triazine derivative, a bisresorcinyl triazine derivative, an imidazoline derivative, a benzylmalonate derivative, a 4,4-diarylbutadiene derivative, a benzoxazole derivative, a merocyanine derivative, a malonitrile or a malonate diphenyl butadiene derivative, a chalcone derivative, and mixtures thereof. It is common to include a plurality of organic UV filters, i.e., two or more organic UV filters. It is also useful to include at least one organic UVA filter (e.g., avobenzone) and at least one organic UVB filter.

The UV filter(s) are typically present in a cosmetically acceptable carrier, which can be water- or oil-based. The sunscreen compositions can be in the form of oil-in-water emulsions, water-in-oil emulsions. Furthermore, in some instances, the sunscreen compositions are not in the form of emulsions; the UV filters may be suspended or dissolved in either a water- or oil-based medium.

The methods are useful for improving the appearance of skin and for protecting the skin from UVA and UVB radiation. The methods include layered application of a skin perfecting composition and a sunscreen composition to the skin, and in particular, the skin of the face and/or neck and may be specifically applied around the eyes, around the mouth, and/or around the neck of a human face. In addition to protecting skin from UVA and UVB radiation, the instant case also encompasses methods for treating or reducing the appearance of wrinkles, blemishes, dryness, roughness, dullness, age spots, discoloration, scarring, sagging, and/or puffiness of skin.

DETAILED DESCRIPTION OF THE DISCLOSURE

The instant case relates to methods for perfecting and protecting skin. The methods protect the skin by improving SPF and UVA-PF and simultaneously perfect the skin by reducing the appearance of imperfections in the skin (e.g., reducing the appearance of wrinkles, eye bags, pores, scarring, dark spots (and uneven skin tone), dark circles, roughness, etc.). The methods comprise layering onto the skin two distinct compositions—a skin perfecting composition and a sunscreen composition. The term "layering" means that the compositions or consecutively applied to the skin, one on top of the other. The order of application is not critical; the skin perfecting composition can be applied first followed by the sunscreen composition, or vice versa. The inventors discovered that layering the skin perfecting composition and the sunscreen composition onto the skin unexpectedly improved the SPF and UVA-PF. Mixing the skin perfecting composition and the sunscreen composition and applying the mixture to the skin did not provide the same improvement in SPF and UVA-PF. In other words, the layered application of the skin perfecting composition and the sunscreen composition increases SPF and UVA-PF more than the SPF and UVA-PF obtained by applying a mixture of the skin perfecting composition and the sunscreen composition in the same ratio as the layered application of the skin perfecting composition and the sunscreen composition.

The methods of the instant case for perfecting and protecting skin comprise layered application of a skin perfecting composition and a sunscreen composition to the skin:
(a) the skin perfecting composition comprising:
(i) about 1 to about 40 wt. %, based on the total weight of the skin perfecting composition, of at least one primary film forming polymer having a Young's modulus of 0.1 to 50 MPa, and elongation at break >50% and a glass transition temperature of <0° C.;
(ii) about 1 to about 35 wt. %, based on the total weight of the skin perfecting composition, of at least one pressure sensitive adhesive polymer;
(iii) about 1 to about 35 wt. %, based on the total weight of the skin perfecting composition, of soft focus powder; and
(iv) water; and
(b) the sunscreen composition comprising:
(i) at least one organic UV filter; and
(ii) a cosmetically acceptable carrier.

The skin perfecting composition may be applied first or the sunscreen composition may be applied first. Similar amounts of the skin perfecting composition and sunscreen composition can be applied. For instance, the ratio of skin perfecting composition to sunscreen composition applied to the skin may be about 3:1 to about 1:3, about 2:1 to about 1:2. In some instances, more skin perfecting composition is applied than the sunscreen composition, such that the ratio of sunscreen composition to skin perfecting composition is about 1:5 to about 1:(greater than 1), about 1:3 to about 1:(greater than 1), about 1:3 to about 1:(greater than 1), or about 1:2 to about 1:(greater than 1). The skin perfecting compositions and the sunscreen compositions can be layered immediately one on top of the other. In some instances, it may be desirable to wait for a period of time before layering the skin perfecting composition or the sunscreen composition on top of the other. For example, it can be useful to allow the initial application of the skin perfecting composition or the sunscreen composition to dry for a period of time before subsequently layering the skin perfecting composition or the sunscreen composition. The period of time may be about 1 second to about 20 minutes, about 10 seconds to about 20 minutes, about 30 seconds to about 20 minutes, or about 1 minute to about 20 minutes.

The skin perfecting composition and sunscreen composition can be layered onto all areas of the body for which protection and perfection is desired. Nonetheless, the methods are particularly useful for treating the skin of the face, which is often exposed to the sunlight.

In addition to the primary film forming polymers, the pressure sensitive adhesive polymers, the soft focus powder, and water, the skin perfecting compositions may optionally include secondary non-polyurethane film forming polymers, thickening agents, water-soluble solvents, etc.

In addition to the organic UV filters and the cosmetically acceptable carrier, the sunscreen composition may optionally include inorganic UV filters, fatty compounds, nonionic emulsifiers, water-soluble solvents, etc.

Methods of using the skin perfecting compositions and the sunscreen compositions of the above embodiment can increase in vitro SPF more than the in vitro SPF obtained by applying a mixture of the skin perfecting compositions and the sunscreen compositions in the same ratio as the layered application of the skin perfecting compositions and the sunscreen compositions. Similarly, methods using the skin perfecting compositions and the sunscreen compositions of the above embodiment can increase in vitro UVA-PF more than the in vitro UVA-PF obtained by applying a mixture of the skin perfecting composition and the sunscreen composition in the same ratio as the layered application of the skin perfecting compositions and the sunscreen compositions.

Primary Film Forming Polymer

The skin perfecting compositions include at least one primary film forming polymer having a Young's modulus of 0.1 to 50 MPa, an elongation at break >50%, and a glass transition temperature of <0° C. These polymers provide a tightening effect to the skin yet retain elasticity and therefore are able to follow facial movements without cracking and peeling.

The Young's modulus may be lower, for example, from 0.1 to about 40 MPa, from 0.1 to 35 MPa, or 0.1 to 30 MPa. The elongation at break can be even higher, for example, >50%, >75%, or >100%. Also, the glass transition temperature may be lower, for example, <−5° C., <−10° C., <−15° C., <−20° C., or <−25° C. In some instances, at least two primary film forming polymers may be present. For example, a first primary film forming polymer may have a Young's modulus of 0.1 to 10 MPa and a second primary film forming polymer may have a Young's modulus of greater than 10 MPa to about 50 MPa, greater than 10 MPa to about 40 MPa, or greater than 10 MPa to about 30 MPa.

Non-limiting examples of useful primary film forming polymers include polyurethane latex polymers, for example, those that are formed by reacting a di- or polyisocyanate with a diol and/or polyol, including for example, aqueous polyurethane dispersions. More specific, non-limiting examples include polyurethane-32, polyurethane-34, polyurethane-35, polyurethane-48, and a mixture thereof. In one embodiment, the cosmetic compositions include at least two primary film forming polymers selected from the group consisting of polyurethane-32, polyurethane-34, polyurethane-35, polyurethane-48, and a mixture thereof, for example polyurethane-34 and polyurethane-35.

The total amount of primary film forming polymers in the cosmetic composition can vary but is typically about 1 to about 40 wt. %, based on the total weight of the skin perfecting composition. In some cases, the total amount of primary film forming polymers is about 1 to about 35 wt. %, about 1 to about 30 wt. %, about 5 to about 40 wt. %, about 5 to about 35 wt. %, about 5 to about 30 wt. %, about 10 to about 40 wt. %, about 10 to about 35 wt. %, or about 10 to about 30 wt. %, based on the total weight of the skin perfecting composition.

In instances where the cosmetic composition includes at least two primary film forming polymers (a first primary film forming polymer and a second primary film forming polymer), the first primary film forming polymer may have a Young's modulus of 0.1 to 10 MPa (and an elongation at break >50% and a glass transition temperature of <0° C.). The total amount of this first primary film forming polymer may be about 1 to about 25 wt. %, about 1 to about 20 wt. %, about 1 to about 15 wt. %, about 5 to about 25 wt. %, about 5 to about 20 wt. %, or about 5 to about 15, based on the total weight of the cosmetic composition. The second primary film forming polymer may have a Young's modulus of greater than 10 MPa to about 50 mPa (and an elongation at break >50% and a glass transition temperature of <0° C.). The total amount of the second primary film forming polymer may be about 1 to about 25 wt. %, about 1 to about 20 wt. %, about 1 to about 15 wt. %, about 5 to about 25 wt. %, about 5 to about 20 wt. %, or about 5 to about 15, based on the total weight of the cosmetic composition. The ratio of the first primary film forming polymer (having a Young's modulus of 0.1 to 10 MPa) to the second primary film forming polymer (having a Young's modulus of greater than 10 MPa to about 50 mPa) may be about 1:5 to about 5:1, about 1:3 to about 3:1, about 1:2 to about 2:1, about 1.5:1 to about 1:1.5, or about 1:1.

Pressure Sensitive Adhesive Polymer

Pressure-sensitive adhesive polymers (also referred to as self-stick adhesive polymers) are adhesive polymeric materials that form a bond when pressure is applied to bind the adhesive polymeric material with the adherend. Heat is typically not required to activate the adhesive behavior. Pressure sensitive adhesive polymers differ from film forming polymers in the skin perfecting compositions because they do not provide extensive film forming properties. Instead, their primary role is to act as an adhesive that binds or holds the skin perfecting composition to the skin.

Non-limiting examples of pressure sensitive adhesive polymers include copolymers of acrylate and methacrylate, rubber-based polymers, and styrene copolymers (such as styrene-isoprene-styrene (SIS) and styrene-butadiene-styrene (SBS) copolymers). In some instances, the pressure sensitive adhesive polymer is an acrylate polymer, for example, a copolymer of butyl acrylate, butyl methacrylate or acrylic acid. A non-limiting examples of such polymer is 2-ethylhexylacrylate (also referred to as (poly)ethylhexylacrylate) (GEL-TAC 100G, GET-TAC 100F, etc. (Advanced Polymer International)).

Non-limiting examples of pressure sensitive adhesive polymers based on rubber include natural rubber (poly(cis-1,4-isoprene)), methyl methacrylate-isoprene graft copolymers, styrene-butadiene copolymer, butyl rubber, acrylonitrile-butadiene rubber, styrene-isoprene block copolymer, polybutadiene, ethylene-butylene block copolymer, and polychloroprene.

Another type of pressure sensitive adhesive polymer that may be used includes those based on polar acrylic polymers. For example, these can include statistical or block copolymers based on acrylic acid, alkyl acrylates, and alkyl methacrylates can be used, as well as copolymers of these acrylics with ethylene and vinyl acetate.

Specifically preferred are copolymers of butyl acrylate, butyl methacrylate, and acrylic acid. These copolymers are commercially available, for example, under the name Roderm 560 (Rohm and Haas). Another preferred pressure sensitive adhesive according to the invention comprises poly(2-ethylhexylacrylate), which is, for example, commercially available under the name Gel-Tac 100G (Advanced Polymer International) as a 40% solids aqueous dispersion of 15 micron tacky acrylic microspheres or Gel-Tac 100F (Advanced Polymer Internation) as a 45% solids aqueous dispersion of 29 micron tacky acrylic microspheres Specific examples of useful acrylic copolymers are commercially available under the trade names EASTAREZ 2010, 2020, and 2050 (Eastman Chemical Co.); ACRONAL V210 (BASF); Mowilith LDM 7255 and Revacryl 491 (Clariant); and FLEXBOND 165 (Air Products). Specific examples of useful rubber polymeric materials (isoprene and butadiene polymers) are commercially available under the trade names RICON 130 polybutadiene (Atofina Sartomer) and ISOLENE 40 polyisoprene (Elementis). Specific examples of useful vinyl acetate copolymers are commercially available under the trade names PVP/VA S-630 (International Specialty Products) and FLEXBOND 149 (Air Products). Specific examples of useful vinyl alcohol/vinyl acetate copolymers are commercially available under the trade names CELVOL 107 (CELANESE) and ELVANOL 50-42 (DuPont).

The total amount of the pressure sensitive adhesive polymer may vary but is typically about 1 to about 35 wt. %, based on the total weight of the skin perfecting composition. In some instance, the total amount of the pressure sensitive adhesive polymer may be about 1 to about 30 wt. %, about 1 to about 25 wt. %, about 1 to about 20 wt. %, about 1 to about 15 wt. %, about 1 to about 10 wt. %, about 2 to about 30 wt. %, about 2 to about 25 wt. %, about 2 to about 20 wt. %, about 2 to about 15 wt. %, about 2 to about 10 wt. %, about 3 to about 30 wt. %, about 3 to about 25 wt. %, about 3 to about 20 wt. %, about 3 to about 15 wt. %, or about 3 to about 10 wt. %, based on the total weight of the skin perfecting composition.

Soft Focus Powder

Soft focus powders are materials that provide a blurring effect, typically due to their light-scattering properties on the skin. Such powders typically have high diffuse reflectance, low specular reflectance, and high diffuse transmittance. Soft focus powders give the skin a smoother appearance, for example, by reducing the difference in luminosity between the valley and the edges of wrinkles and imperfections.

Non-limiting examples of soft focus powders include powders of natural or synthetic origin such as mica, titanated mica, alumina, aluminum silicate, silica which may or may not be coated, fumed silica, silica silylate, titanium dioxide, serecite, composite talc/titanium dioxide/alumina/silica powders, polyamide, poly(methyl (meth)acrylate), polyethylene powder, polymethylsilsesquioxane powder, and a mixture thereof. Additional non-limiting examples include calcium aluminum borosilicate (LUXSIL), PMMA (Microsphere M-100), polyethylene (POLYETHYLENE CI 2080), methyl methacrylate crosspolymer (COVABEADS LH85), nylon-12 (ORGASOL 2002), or ethylene/acrylic acid copolymer (FLOBEADS EA209). In some instances, the cosmetic compositions include at least one soft focus powder selected from the group consisting of silica which may or may not be coated, fumed silica, silica silylate, composite talc/titanium dioxide/alumina/silica powders, polyamide (nylon), poly(methyl (meth)acrylate), polyethylene powder, polymethylsilsesquioxane powder, and a mixture thereof.

In certain instances, the soft focus powers are copolymers of polydimethylsiloxane, for example, high molecular weight copolymers of polydimethylsiloxane. Non-limiting examples include divinyldimethicone/dimethicone copolymers, such as HMW 2200 from Dow Corning (divinyldimethicone/dimethicone copolymer (and) C12-12 Pareth-3 (and) C12-13 Pareth-2.

The total amount of soft focus powder can vary but is typically about 1 to about 35 wt. %, based on the total weight of the skin perfecting composition. In some cases, the total amount of soft focus powder is about 1 to about 30 wt. %, about 1 to about 25 wt. %, about 1 to about 20 wt. %, about 5 to about 35 wt. %, about 5 to about 30 wt. %, about 5 to about 25 wt. %, about 5 to about 20 wt. %, about 10 to about 35 wt. %, about 10 to about 30 wt. %, about 10 to about 25 wt. %, or about 10 to about 20 wt. %, based on the total weight of the skin perfecting composition.

Water

The total amount of water in the skin perfecting compositions can vary but is typically about 10 to about 90 wt. %, based on the total weight of the skin perfecting composition. Additionally, the total amount of water may be about 20 to about 80 wt. %, about 25 to about 75 wt. %, about 30 to about 70 wt. %, about 35 to about 65 wt. %, or about 40 to about 60 wt. %, based on the total weight of the skin perfecting composition.

Optional Secondary Non-Polyurethane Film Forming Polymers

At least one secondary, non-polyurethane film forming polymer may also optionally be included in the cosmetic compositions. The optional, secondary, non-polyurethane film forming polymers, if present, typically have a glass transition temperature of <25° C. Furthermore, the glass transition of the at least one primary film forming polymer and the at least one secondary film forming polymer, if present, typically differs by at least 20° C. The glass transition of the at least one primary film forming polymer and the at least one secondary film forming polymer, if present, may differ by at least 30° C., 40° C., 50° C., 60° C., 70° C., or 80° C. A maximum difference between glass transition temperatures may be 50° C., 60° C., 70° C., 80° C. or 100° C. In addition to its film forming properties, the secondary, non-polyurethane film forming polymer can be helpful in providing a variety of other beneficial properties to the cosmetic compositions, for example, adhesiveness, texture, and durability.

Non-limiting examples of secondary, non-polyurethane film forming polymer include acrylic polymers or co-polymers, acrylates, polyolefins, polyvinyls, polacrylates, silicones, polyamides, polyethers, polyesters, fluoropolymers, polyethers, polyacetates, polycarbonates, polyamides, polyimides, rubbers, epoxies, formaldehyde resins, organosiloxanes, dimethicones, methicones, cellulosics, polysaccharides, polyquaterniums, and the like. Suitable film formers include those listed in the Cosmetic Ingredient Dictionary (INCI and Handbook, 12$^{th}$ Edition (2008), the disclosure of which is hereby incorporated by reference.

In some instance, the at least one secondary, non-polyurethane film forming polymer is an acrylate polymer. Non-limiting examples include acrylates copolymer, styrene/acrylates copolymer, acarylates/ethylhexyl acrylate copolymer, an alkyl acrylate copolymer, acrylic copolymers, polyacrylate-2 crosspolymer, acrylates/hydroxyesters acrylate copolymer, acrylate/ethylhexyl acrylate copolymer, styrene acrylate copolymer, acrylate/VA copolymer, styrene/acrylic copolymer, styrene/acrylates copolymer, styrene/acrylates/ammonium methacrylate copolymer, and a mixture thereof.

Additional non-limiting examples of film forming polymers include but are not limited to: from Kobo Products Inc., DIATOSOL products (e.g., styrene/acrylates copolymer, acarylates/ethylhexyl acrylate copolymer, alkyl acrylate copolymer, etc.), from Dow Chemical Company, EPITEX products (acrylates copolymer), from Interpolymer, SYNTRAN products (acrylic copolymers), from Akzo Nobel Surface Chemistry LLC, Bridgewater N.J., AMPHOMER and AMPHOMER LV-71 polymers (octylacrylamide/acrylates/butylaminoethyl methacrylate compolymer), AMPHOMER HC polymer (acrylates/octylacrylamide copolymer) BALANCE 0/55, BALANCE CR and DERMACRYL AQF polymers (acrylates copolymer), BALANCE 47 polymer (octylacrylamide/butylaminoethyl methacrylate copolymer), RESYN 28-2930 polymer (VA/crotonates/vinyl neodecanoate copolymer), RESYN 28-1310 polymer (VA/Crotonates copolymer), FLEXAN polymers (sodium polystyrene sulfonate), DynamX polymer (polyurethane-14 (and) AMP-Acrylates copolymer), RESYN XP polymer (acrylates/octylacrylamide copolymer), STRUCTURE 2001 (acrylates/steareth-20 itaconate copolymer) and STRUCTURE 3001 (acrylates/ceteth-20 itaconate copolymer); from ISP, OMNIREZ-2000 (PVM/MA half ethyl ester copolymer), GANEX P-904 (butylated PVP), GANEX V-216 (PVP/hexadecene copolymer) GANEX V-220 (PVP/eicosene copolymer), GANEX WP-660 (tricontanyl PVP), GANTREZ A425 (butyl ester of PVM/MA copolymer), GANTREZ AN-119 PVM/MA copolymer, GANTREZ ES 225 (ethyl ester of PVM/MA copolymer), GANTREZ ES425 (butyl ester of PVM/MA copolymer), GAFFIX VC-713 (vinyl caprolactam/PVP/dimethylaminoethyl methacrylate copolymer), GAFQUAT 755 (polyquaternium-11), GAFQUAT HS-100 (polyquaternium-28) AQUAFLEX XL-30 (Polyimide-1), AQUAFLEX SF-40 (PVP/Vinylcaprolactam/DMAPA Acrylates Copolymer), AQUAFLEX FX-64 (Isobutylene/Ethylmaleimide/Hydroxyethylmaleimide Copolymer), ALLIANZ LT-120 (Acrylates/C1-2 Succinates/Hydroxyacrylates Copolymer), STYLEZE CC-10 (PVP/DMAPA Acrylates Copolymer), STYLEZE 2000 (VP/Acrylates/Lauryl Methacrylate Copolymer), STYLEZE W-20 (Polyquaternium-55), Copolymer Series (PVP/Dimethylaminoethylmethacrylate Copolymer), ADVANTAGE S and ADVANTAGE LCA (VinylcaprolactamNP/Dimethylaminoethyl Methacrylate Copolymer), ADVANTAGE PLUS (VA/Butyl Maleate/Isobornyl Acrylate Copolymer); from BASF, ULTRAHOLD STRONG (acrylic acid/ethyl acrylate/t-butyl acrylamide), LUVIMER 100P (t-butyl acrylate/ethyl acrylate/methacrylic acid), LUVIMER 36D (ethyl acrylate/t-butyl acrylate/methacrylic acid), LUVIQUAT HM-552 (polyquaternium-16), LUVI- QUAT HOLD (polyquaternium-16), LUVISKOL K30 (PVP) LUVISKOL K90 (PVP), LUVISKOL VA 64 (PVPNA copolymer) LUVISKOL VA73W (PVPNA copolymer), LUVISKOL VA, LUVISET PUR (Polyurethane-1), LUVISET Clear (VP/MethacrylamideNinyl Imidazole Copolymer), LUVIFLEX SOFT (Acrylates Copolymer), ULTRAHOLD 8 (Acrylates/Acrylamide Copolymer), LUVISKOL Plus (Polyvinylcaprolactam), LUVIFLEX Silk (PEG/PPG-25/25 Dimethicone/Acrylates Copolymer); from Amerchol, AMERHOLD DR-25 (acrylic acid/methacrylic acid/acrylates/methacrylates); from Rohm&Haas, ACUDYNE 258 (acrylic acid/methacrylic acid/acrylates/methacrylates/hydroxyl ester acrylates; from Mitsubishi and distributed by Clariant, DIAFORMER Z-301, DIAFORMER Z-SM, and DIAFORMER Z-400 (methacryloyl ethyl betaine/acrylates copolymer), ACUDYNE 180 (Acrylates/Hydroxyesters Acrylates Copolymer), ACUDYNE SCP (Ethylenecarboxyamide/AMPSA/Methacrylates Copolymer), and the ACCULYN rheological modifiers; from ONDEO Nalco, FIXOMER A-30 and FIXOMER N-28 (INCI names: methacrylic acid/sodium acrylamidomethyl propane sulfonate copolymer); from Noveon, FIXATE G-100 (AMP-Acrylates/Allyl Methacrylate Copolymer), FIXATE PLUS (Polyacrylates-X), CARBOPOL Ultrez 10 (Carbomer), CARBOPOL Ultrez 20 (Acrylates/C10-30 Alkyl Acrylates Copolymer), AVALURE AC series (Acrylates Copolymer), AVALURE UR series (Polyurethane-2, Polyurethane-4, PPG-17/IPDI/DMPA Copolymer); polyethylene glycol; water-soluble acrylics; water-soluble polyesters; polyacrylamides; polyamines; polyquaternary amines; styrene maleic anhydride (SMA) resin; polyethylene amine; and other conventional polymer that is polar solvent soluble or that can be made soluble through neutralization with the appropriate base.

The total amount of the secondary, non-polyurethane film forming polymers, if present, may vary but is typically about 1 to about 35 wt. %, based on the total weight of the skin perfecting composition. In some instances, the total amount of the secondary film forming polymer may be about 1 to about 30 wt. %, about 1 to about 25 wt. %, about 1 to about 20 wt. %, about 1 to about 15 wt. %, about 1 to about 10 wt. %, about 2 to about 30 wt. %, about 2 to about 25 wt. %, about 2 to about 20 wt. %, about 2 to about 15 wt. %, about 2 to about 10 wt. %, about 3 to about 30 wt. %, about 3 to about 25 wt. %, about 3 to about 20 wt. %, about 3 to about 15 wt. %, or about 3 to about 10 wt. %, based on the total weight of the skin perfecting composition.

Thickening Agents

At least one thickening agent (also referred to as thickeners or viscosity modifying agents) can be included in the compositions. In some instances, the compositions include at least one hydrophilic thickening agent. Non-limiting examples include modified or unmodified carboxyvinyl polymers (e.g., carbomer), acrylates/C10-30 alkyl acrylate crosspolymer, polyacrylates, polymethacrylates, polyacrylamides, optionally crosslinked and/or neutralized 2-acrylamido-2-methylpropane sulfonic acid polymers (e.g., ammonium polyacryldimethyltauramide), crosslinked anionic copolymers of acrylamide and of 2-acrylamido-2-methylpropane sulfonic acid (AMPS) (e.g., acrylamide/sodium acryloyldimethyltaurate copolymer), polysaccharides (e.g., xanthan gum, guar gum, carob gum, acacia gum, scleroglucans, chitin and chitosan derivatives, carranenans, gellans, alginates), celluloses (e.g., microcrystalline cellulose, carboxymethylcellulose, hydroxymethylcellulose and hydroxypropylcellulose), and a mixture thereof. In some instances, a preferred thickening agent is a crosslinked anionic copolymer of acrylamide and of 2-acrylamido-2-methylpropane sulfonic acid (AMPS) (e.g., acrylamide/sodium acryloyldimethyltaurate copolymer).

Additional non-limiting examples of hydrophilic thickening agents include polyvinylpyrrolidone (PVP), polyvinyl alcohol, crosslinked acrylates (e.g. CARBOPOL 982), hydrophobically-modified acrylates (e.g. Carbopol 1382); polyacrylamides such as, for example, the crosslinked copolymers sold under the names Sepigel 305 (CTFA name: polyacrylamide/C13-C14 isoparaffin/Laureth 7) or SIMULGEL 600 (CTFA name: acrylamide/sodium acryloyldimethyltaurate copolymer/isohexadecane/polysorbate 80) by SEPPIC; 2-acrylamido-2-methylpropanesulphonic acid polymers and copolymers, that are optionally crosslinked and/or neutralized; cellulose derivatives such as hydroxyethylcellulose, sodium carboxymethylcellulose, hydroxypropyl methylcellulose, hydroxypropyl cellulose, ethyl cellulose and hydroxymethyl cellulose; polysaccharides and gums, e.g., natural gums such as xanthan gum, sclerotium, carrageenan and pectin; polysaccharide resins such as starch and its derivatives, hyaluronic acid and its salts, clays, and, in particular, montmorillonites, hectorites, bentonites, and laponites, crosslinked polyacrylic acids, such as the "CARBOPOL" products from the company Goodrich, the polyglyceryl(meth)acrylates polymers sold under the names "HISPAGEL" or "LUBRAGEL" by the companies Hispano Quimica or Guardian, crosslinked acrylamide polymers and copolymers, such as those sold under the names "PAS 5161" or "BOZEPOL C" by the company Hoechst, "SEPIGEL 305" by the company SEPPIC, crosslinked methacryloyloxyethyltrimethylammonium chloride homopolymers sold under the name "SALCARE SC95" by the company Allied Colloid, and a mixture thereof.

The one or more thickening agents may be xanthan gum, guar gum, biosaccharide gum, cellulose, acacia Seneca gum, sclerotium gum, agarose, pechtin, gellan gum, hyaluronic acid. Additionally, the one or more thickeners may include polymeric thickeners selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the thickening agent includes ammonium polyacryloyldimethyl taurate and/or sodium polyacrylate.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerythritol. The carbomers are available as the CARBOPOL 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 4,599,379 and EP 228,868, which are all incorporated herein by reference in their entirety.

c. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturizing gels of the type as exemplified by the product range called Lubrajel® from United Guardian. These gels have moisturizing, viscosifying, stabilizing properties.

d. Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

e. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, biosacharide gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived form callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

The total amount of thickening agent, if present, in the skin perfecting composition can vary but is typically about 0.01 to about 10 wt. %, based on the total amount of the skin perfecting composition. In some cases, the total amount of thickening agent is about 0.01 to about 5 wt. %, about 0.01 to about 2 wt. %, about 0.1 to about 10 wt. %, about 0.1 to about 5 wt. %, about 0.1 to about 2 wt. %, or about 0.1 to about 1 wt. %, based on the total weight of the skin perfecting composition.

The total amount of thickening agent, if present, in the sunscreen composition can vary but is typically about 0.01 to about 10 wt. %, based on the total amount of the skin perfecting composition. In some cases, the total amount of thickening agent is about 0.01 to about 5 wt. %, about 0.01 to about 2 wt. %, about 0.1 to about 10 wt. %, about 0.1 to about 5 wt. %, about 0.1 to about 2 wt. %, or about 0.1 to about 1 wt. %, based on the total weight of the sunscreen composition.

Water-Soluble Solvents

The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvent has a solubility of at least 60%, 70%, 80%, or 90%. Non-limiting examples of water-soluble solvents include, for example, glycerin, $C_{1-4}$ alcohols, organic solvents, fatty alcohols, fatty ethers, fatty esters, polyols, glycols, and any a mixture thereof. In some instances, the cosmetic composition includes one or more $C_{1-4}$ alcohols, for example, ethanol.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the water-soluble solvent, if present, in the skin perfecting compositions may vary but is typically about 0.01 to about 25 wt. %, based on the total weight of the skin perfecting composition. In some cases, the total amount of water-soluble solvents is about 0.01 to about 20 wt. %, about 0.01 to about 15 wt. %, about 0.01 to about 10 wt. %, about 0.1 to about 25 wt. %, about 0.1 to about 20 wt. %, about 0.1 to about 15 wt. %, about 0.1 to about 10 wt. %, about 1 to about 25 wt. %, about 1 to about 20 wt. %, about 1 to about 15 wt. %, about 1 to about 10 wt. %, or about 1 to about 8 wt. %, based on the total weight of the skin perfecting composition.

The total amount of the water-soluble solvent, if present, in the sunscreen compositions may vary but is typically about 0.01 to about 25 wt. %, based on the total weight of the sunscreen composition. In some cases, the total amount of water-soluble solvents is about 0.01 to about 20 wt. %, about 0.01 to about 15 wt. %, about 0.01 to about 10 wt. %, about 0.1 to about 25 wt. %, about 0.1 to about 20 wt. %, about 0.1 to about 15 wt. %, about 0.1 to about 10 wt. %, about 1 to about 25 wt. %, about 1 to about 20 wt. %, about 1 to about 15 wt. %, about 1 to about 10 wt. %, or about 1 to about 8 wt. %, based on the total weight of the sunscreen composition.

UV Filters

UV filters are well known in the art for their use in protection from UV radiation. For example, the UV filter may be one or more organic UV filters and/or one or more inorganic UV filters. Non-limiting examples of UV filters include:

i. Sparingly soluble UV filters (not appreciably soluble in either water or oil) such as Methylene Bis-Benzotriazolyl Tetramethylbutylphenol, Tris-Biphenyl Triazine, Methanone, 1,1'-(1,4-piperazinediyl)bis[1-[2-[4-(diethylamino)-2-hydroxybenzoyl]phen-yl]-and mixtures thereof.

ii. Oil soluble organic UV filters (at least partially soluble in oil or organic solvent), such as Bis-Ethylhexyloxyphenol Methoxyphenyl Triazine, Butyl Methoxydibenzoylmethane (BMBM), Oxybenzone, Sulisobenzone, Diethylhexyl Butamido Triazone (DBT), Drometrizole Trisiloxane, Ethylhexyl Methoxycinnamate (EHMC), Ethylhexyl Salicylate (EHS), Ethylhexyl Triazone (EHT), Homosalate, Isoamyl p-Methoxycinnamate, 4-Methylbenzylidene Camphor, Octocrylene (OCR), Polysilicone-15, and Diethylamino Hydroxy Benzoyl Hexyl Benzoate (DHHB);

iii. Inorganic UV filters such as titanium oxide and zinc oxide, iron oxide, zirconium oxide and cerium oxide; and iv. Water soluble UV filters such as Phenylbenzimidazole Sulfonic Acid (PBSA), Sulisobenzone-sodium salt, Benzydilene Camphor Sulfonic Acid, Camphor Benzalkonium Methosulfate, Cinoxate, Disodium Phenyl Dibenzylmidazole Tetrasulfonate, Terephthalylidene Dicamphor Sulfonic Acid, PABA, and PEG-25 PABA.

In some instances, the UV filter is one or more of: a para-aminobenzoate derivative, a salicylate derivative, a cinnamate derivative, a benzophenone or an aminobenzophenone, an anthranillate derivative, a β,β-diphenylacrylate derivative, a benzylidenecamphor derivative, a phenylbenzimidazole derivative, a benzotriazole derivative, a triazine derivative, a bisresorcinyl triazine derivative, an imidazoline derivative, a benzylmalonate derivative, a 4,4-diarylbutadiene derivative, a benzoxazole derivative, a merocyanine derivative, malonitrile or a malonate diphenyl butadiene derivative, a chalcone derivative, or mixtures thereof.

Suitable UV filters can include broad-spectrum UV filters that protect against both UVA and UVB radiation, or UV filters that protect against UVA or UVB radiation. In some instances, the one or more UV filters may be methylene bis-benzotriazolyl tetramethylphenol, diethylamino hydroxybenzoyl hexyl benzoate, coated or uncoated zinc oxide, ethylhexyl methoxycinnamate, isoamyl methoxycinnamate, homosalate ethyl hexyl salicilate, octocrylene, polysilicone-15, butyl methoxydibenzoylmethane, menthyl anthranilate, and ethylhexyl dimethyl PABA.

The total amount of UVA filters (both UVA1 and UVA2) in the sunscreen compositions, if present, may vary but is typically greater than zero to about 20 wt. %, based on the total weight of the sunscreen composition. In some cases, the total amount of UVA filters in the cosmetic compositions is from about 0.01 to about 20 wt. %, about 0.01 to about 15 wt. %, about 0.01 to about 10 wt. %, about 0.01 to about 8 wt. %, about 0.01 to about 6 wt. %, about 0.01 to about 5 wt. %, about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 1 to about 20 wt. %, about 1 to about 15 wt. %, about 1 to about 10 wt. %, about 1 to about 8 wt. %, about 1 to about 6 wt. %, or about 1 to about 5 wt. %, based on the total weight of the cosmetic composition.

The sunscreen compositions include at least one organic UVB filter. In some instances, it is preferable to include more than one organic UVB filter, for example, at least 2, 3, 4, or 5 UVB filters. Non-limiting examples of UVB filters include a para-aminobenzoic acid derivative, a salicylic derivative, a cinnamic derivative, a benzophenone or an aminobenzophenone derivative, an anthranillate derivative, a β,β-diphenylacrylate derivative, a benzylidenecamphor derivative, a phenylbenzimidazole derivative, a benzotriazole derivative, a triazine derivative, a bisresorcinyl triazine derivative, an imidazoline derivative, a benzylmalonate derivative, a 4,4-diarylbutadiene derivative, a benzoxazole derivative, a merocyanine derivative, malonitrile or a malonate diphenyl butadiene derivative, a chalcone derivative, and mixtures thereof.

In some instances, at least one UVB filter may be selected from the group consisting of methylene bis-benzotriazolyl tetramethylphenol (Tinosorb M), diethylamino hydroxybenzoyl hexyl benzoate, ethylhexyl salicylate, ethylhexyl methoxycinnamate, isoamyl methoxycinnamate, polysilicone-15, menthyl anthranilate, ethylhexyl dimethyl PABA, aminobenzoic acid (PABA), cinoxate, dioxybenzone, ecamsule (Mexoryl SX), ensulizole (phenylbenzimiazole sulfonic acid), homosalate, meradimate (menthyl anhranilate), octocrylene, octinoxate (octyl methoxycinnamate), octisalate (octyl salicylate), oxybenzone, padimate O, sulisobenzone, trolamine salicylate, and mixtures thereof.

The sunscreen compositions of the present disclosure may optionally include one or more inorganic UV filters that provide protection from UVA and/or UVB radiation. In some instances, however, the sunscreen compositions of the present disclosure are free or essentially free of inorganic UVA and/or inorganic UVB filters.

The total amount of UVB filters in the sunscreen compositions of the present disclosure can vary and will depend on the desired SPF for the sunscreen composition. Higher amounts of UVB filters typically provide higher SPFs. In some instances, the total amount of UVB filters in the sunscreen compositions may be about 0.1 to about 40 wt. %, based on the total weight of the cosmetic composition. The total amount of UVB filters may be about 0.1 to about 35 wt. %, about 0.1 to about 30 wt. %, about 0.1 to about 25 wt. %, about 0.1 to about 20 wt. %, about 0.1 to about 15 wt. %, about 0.1 to about 10 wt. %, about 1 to about 40 wt. %, about 1 to about 35 wt. %, about 1 to about 30 wt. %, about 1 to about 25 wt. %, about 1 to about 20 wt. %, about 1 to about 15 wt. %, about 1 to about 10 wt. %, about 5 to about 40 wt. %, about 5 to about 35 wt. %, about 5 to about 30 wt. %, about 5 to about 25 wt. %, about 5 to about 20 wt. %, about 5 to about 15 wt. %, or about 5 to about 10 wt. %, based on the total weight of the sunscreen composition.

Cosmetically Acceptable Carrier

The sunscreen compositions include a cosmetically acceptable carrier. The phrase "cosmetically acceptable" means that the material is compatible with skin. For example, "cosmetically acceptable carrier" means a carrier that is compatible with skin and acceptable for application to the skin of the body, especially the skin of the face.

The cosmetically acceptable carrier may include, for example, water and/or water soluble solvents. Non-limiting examples of cosmetically acceptable carriers include glycerin, C1-4 alcohols, organic solvents, fatty alcohols, fatty ethers, fatty esters, polyols, glycols, vegetable oils, mineral oils, liposomes, laminar lipid materials, water, or any combinations thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

Embodiments

In some embodiments, the skin perfecting compositions and the sunscreen compositions may be as follows. The skin perfecting compositions may include:

(i) about 1 to about 40 wt. %, about 5 to about 40 wt. %, or about 5 to about 30 wt. %, based on the total weight of the skin perfecting composition, of at least one primary film forming polymer having a Young's modulus of 0.1 to 50 MPa, an elongation at break >50% and a glass transition temperature of <0° C., for example at least one polyurethane latex polymer such as polyurethane-34 and/or polyurethane-35;

(ii) about 1 to about 35 wt. %, about 1 to about 25 wt. %, or about 1 to about 15 wt. %, based on the total weight of the skin perfecting composition, of at least one pressure sensitive adhesive polymer, for example, a pressure sensitive adhesive acrylate polymer that is a copolymer of butyl acrylate, butyl methacrylate or acrylic acid (e.g., 2-ethylhexylacrylate);

(iii) about 1 to about 35 wt. %, about 1 to about 20 wt. %, or about 5 to about 20 wt. %, based on the total weight of the skin perfecting composition, of soft focus powder, for example, talc, mica, titanated mica, alumina, aluminum silicate, silica which may or may not be coated, fumed silica, silica silylate, polyamide, poly (methyl (meth)acrylate), polyethylene powder, polymethylsilsesquioxane powder, and a mixture thereof;

(iv) about 25 to about 75 wt. %, about 30 to about 70 wt. %, or about 35 to about 75 wt. % of water;

(v) optionally, about 0.01 to about 10 wt. %, about 0.01 to about 5 wt. %, or about 0.1 to about 5 wt. %, based on the total weight of the skin perfecting composition, of at least one thickening agent, for example acrylamide/sodium acryloyldimethyltaurate copolymer; and (vi) optionally, about 0.01 to about 25 wt. %, about 0.1 to about 20, or about 1 to about 10 wt. %, based on the total weight of the skin perfecting composition, of at least one water soluble solvent, for example, glycerin, a C1-4 alcohol, an organic solvent, a polyol, a glycol, and a mixture thereof.

The sunscreen compositions may include:

(i) about 1 to about 40 wt. %, preferably about 5 to about 35 wt. %, more preferably about 10 to about 30 wt. %, based on the total weight of the sunscreen composition, of at least one (and preferably a plurality of) organic UV filters selected from a para-aminobenzoate derivative, a salicylate derivative, a cinnamate derivative, a benzophenone or an aminobenzophenone, an anthranillate derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and a mixture thereof, wherein the sunscreen composition preferably includes at least one UVA filter and at least one UVB filter, thereby providing full spectrum protection from UV radiation; and (ii) about 30 to about 90 wt. %, preferably about 40 to about 85 wt. %, based on the total weight of the sunscreen composition, of more preferably about 50 to about 80 wt. % of a cosmetically acceptable carrier.

In the above embodiment, the skin perfecting composition may be applied first or the sunscreen composition may be applied first. Similar amounts of the skin perfecting composition and sunscreen composition can be applied. For instance, the ratio of skin perfecting composition to sunscreen composition applied to the skin may be about 3:1 to about 1:3, about 2:1 to about 1:2. In some instances, more sunscreen composition is applied than skin perfecting composition, such that the ratio of skin perfecting composition to sunscreen composition is about 1:5 to about 1:(greater than 1), about 1:3 to about 1:(greater than 1), about 1:3 to about 1:(greater than 1), or about 1:2 to about 1:(greater than 1). The skin perfecting compositions and the sunscreen compositions can be layered immediately one on top of the other.

In some instances, it may be desirable to wait for a period of time before layering the skin perfecting composition or the sunscreen composition on top of the other. For example, it can be useful to allow the initial application of the skin perfecting composition or the sunscreen composition to dry for a period of time before subsequently layering the skin perfecting composition or the sunscreen composition. The period of time may be about 1 second to about 20 minutes, about 10 seconds to about 20 minutes, about 30 seconds to about 20 minutes, or about 1 minute to about 20 minutes. The period of time may be about 1 second to about 15 minutes, about 10 seconds to about 15 minutes, about 30 seconds to about 20 minutes or about 1 minute to about 15 minutes.

The skin perfecting composition and sunscreen composition can be layered onto all areas of the body for which protection and perfection is desired. Nonetheless, the methods are particularly useful for treating the skin of the face, which is often exposed to the sunlight.

Methods of using the skin perfecting compositions and the sunscreen compositions of the above embodiment can increase in vitro SPF more than the in vitro SPF obtained by applying a mixture of the skin perfecting compositions and the sunscreen compositions in the same ratio as the layered application of the skin perfecting compositions and the sunscreen compositions. Similarly, methods using the skin perfecting compositions and the sunscreen compositions of the above embodiment can increase in vitro UVA-PF more than the in vitro UVA-PF obtained by applying a mixture of the skin perfecting composition and the sunscreen composition in the same ratio as the layered application of the skin perfecting compositions and the sunscreen compositions.

In another embodiment, the skin perfecting compositions and the sunscreen compositions may be as follows. The skin perfecting compositions may include:

(i) about 1 to about 40 wt. %, about 5 to about 40 wt. %, or about 5 to about 30 wt. %, based on the total weight of the skin perfecting composition, of polyurethane-34 and/or polyurethane-35;

(ii) about 1 to about 35 wt. %, about 1 to about 25 wt. %, or about 1 to about 15 wt. %, based on the total weight of the skin perfecting composition, of a copolymer of butyl acrylate, butyl methacrylate, or acrylic acid (e.g., 2-ethylhexylacrylate);

(iii) about 1 to about 35 wt. %, about 1 to about 20 wt. %, or about 5 to about 20 wt. %, based on the total weight of the skin perfecting composition of polymethylsilsesquioxane powder;

(iv) about 25 to about 75 wt. %, about 30 to about 70 wt. %, or about 35 to about 75 wt. % of water;

(v) about 0.01 to about 10 wt. %, about 0.01 to about 5 wt. %, or about 0.1 to about 5 wt. %, based on the total weight of the skin perfecting composition, of at least one thickening agent, for example acrylamide/sodium acryloyldimethyltaurate copolymer; and (vi) about 0.01 to about 25 wt. %, about 0.1 to about 20, or about 1 to about 10 wt. %, based on the total weight of the skin perfecting composition, of at least one water soluble solvent, for example, glycerin, a C1-4 alcohol, an organic solvent, a polyol, a glycol, and a mixture thereof.

The sunscreen compositions may include:

(i) about 1 to about 40 wt. %, preferably about 5 to about 35 wt. %, more preferably about 10 to about 30 wt. %, based on the total weight of the sunscreen composition, of at least one (and preferably a plurality of) two or more organic UV filters selected from a para-aminobenzoate derivative, a salicylate derivative, a cinnamate derivative, a benzophenone or an aminobenzophenone, an anthranillate derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and a mixture thereof, wherein the sunscreen composition includes at least one UVA filter and at least one UVB filter, thereby providing full spectrum protection from UV radiation; and (ii) about 30 to about 90 wt. %, preferably about 40 to about 85 wt. %, based on the total weight of the sunscreen composition, of more preferably about 50 to about 80 wt. % of a cosmetically acceptable carrier.

In the above embodiment, the skin perfecting composition may be applied first or the sunscreen composition may be applied first. Similar amounts of the skin perfecting composition and sunscreen composition can be applied. For instance, the ratio of skin perfecting composition to sunscreen composition applied to the skin may be about 3:1 to about 1:3, about 2:1 to about 1:2. In some instances, more sunscreen composition is applied than skin perfecting composition, such that the ratio of skin perfecting composition to sunscreen composition is about 1:5 to about 1:(greater than 1), about 1:3 to about 1:(greater than 1), about 1:3 to about 1:(greater than 1), or about 1:2 to about 1:(greater than 1). The skin perfecting compositions and the sunscreen compositions can be layered immediately one on top of the other.

In some instances, it may be desirable to wait for a period of time before layering the skin perfecting composition or the sunscreen composition on top of the other. For example, it can be useful to allow the initial application of the skin perfecting composition or the sunscreen composition to dry for a period of time before subsequently layering the skin perfecting composition or the sunscreen composition. The period of time may be about 1 second to about 20 minutes, about 10 seconds to about 20 minutes, about 30 seconds to about 20 minutes, or about 1 minute to about 20 minutes. The period of time may be about 1 second to about 15 minutes, about 10 seconds to about 15 minutes, about 30 seconds to about 20 minutes or about 1 minute to about 15 minutes.

The skin perfecting composition and sunscreen composition can be layered onto all areas of the body for which protection and perfection is desired. Nonetheless, the methods are particularly useful for treating the skin of the face, which is often exposed to the sunlight.

Methods of using the skin perfecting compositions and the sunscreen compositions of the above embodiment can increase in vitro SPF more than the in vitro SPF obtained by applying a mixture of the skin perfecting compositions and the sunscreen compositions in the same ratio as the layered application of the skin perfecting compositions and the sunscreen compositions. Similarly, methods using the skin perfecting compositions and the sunscreen compositions of the above embodiment can increase in vitro UVA-PF more than the in vitro UVA-PF obtained by applying a mixture of the skin perfecting composition and the sunscreen composition in the same ratio as the layered application of the skin perfecting compositions and the sunscreen compositions.

Implementation of the present disclosure is provided by way of the following examples. The examples serve to illustrate the technology without being limiting in nature.

Example 1

Skin Perfecting Compositions A and B

| Skin Perfecting Composition | | A |
|---|---|---|
| | INCI US | |
| Film Forming Polymer | POLYURETHANE-34 | 24.5 |
| Pressure Sensitive Adhesive (PSA) Polymer | POLYETHYLHEXYL ACRYLATE (Polymer of the monomer 2-ethylhexyl acrylate) | 4.5 |
| Soft Focus Powder | POLYMETHYLSILSESQUIOXANE AND/OR SILICA | 8.5 |

-continued

| Skin Perfecting Composition | | A |
|---|---|---|
| Thickening Agent | ACRYLAMIDE/SODIUM ACRYLOYLDIMETHYLTAURATE COPOLYMER | 0.4 |
| Water-Soluble Solvent | ALCOHOL DENAT. | 3 |
| | METHYLPROPANEDIOL | 0.9 |
| | CAPRYLYL GLYCOL | 0.2 |
| Solvent | ISOHEXADECANE | 0.2 |
| | ETHYLHEXYLGLYCERIN | 0.1 |
| Nonionic Surfactant | POLYSORBATE 80 | 0.1 |
| | SORBITAN OLEATE | 0.02 |
| Silicone | PEG-12 DIMETHICONE | 0.5 |
| Miscellaneous | PRESERVATIVE(S), FRAGRANCE(S), CHELATING AGENT(S), VITAMIN(S), ETC. | ≤3 |
| Carrier | WATER | 56.6 |

| Skin Perfecting Composition | | B |
|---|---|---|
| | INCI US | |
| Film Forming Polymer | POLYURETHANE-34 | 11.4 |
| Film Forming Polymer | POLYURETHANE-35 | 11.4 |
| Film Forming Polymer | ACRYLATES COPOLYMER | 4.5 |
| Pressure Sensitive Adhesive (PSA) Polymer | 2-ETHYLHEXYL ACRYLATE (Polymer of the monomer 2-ethylhexyl acrylate) | 4.5 |
| Soft focus powders | POLYMETHYLSILSESQUIOXANE AND/OR SILICA | 13 |
| Thickening Agent | ACRYLAMIDE/SODIUM ACRYLOYLDIMETHYLTAURATE COPOLYMER | 0.4 |
| Solvent | ISOHEXADECANE | 0.2 |
| Water-Soluble Solvent | ALCOHOL DENAT. | 3 |
| Nonionic Surfactant | LAURETH-21, POLYSORBATE 80, & SORBITAN OLEATE | ≤1 |
| Preservatives | PRESERVATIVES | ≤1 |
| Water | WATER | QS 100 |

Example 2

Sunscreen Compositions C and D

| Sunscreen (Oil-in-Water Emulsion) | | C |
|---|---|---|
| | INCI US | |
| UVA Filter | AVOBENZONE | 3 |
| UVB Filters | HOMOSALATE | 5 |
| | ETHYLHEXYL SALICYLATE | 4 |
| | OCTOCRYLENE | 5 |
| Nonionic Emulsifier | GLYCERYL STEARATE (and) PEG-100 STEARATE | 3 |
| Thickening Agent | ACRYLATES COPOLYMER | 0.4 |
| pH Adjustment | TRIETHANOLAMINE | 0.2 |
| Miscellaneous | PRESERVATIVE(S), CHELATING AGENT(S), VITAMIN(S), ETC. | ≤3 |
| Carrier | WATER | 75.8 |

| Sunscreen (Water-in-Oil Emulsion) | | D |
|---|---|---|
| UVA Filter | INCI US AVOBENZONE | 3 |
| UVB Filters | HOMOSALATE | 5 |
| | ETHYLHEXYL SALICYLATE | 5 |
| | OCTOCRYLENE | 7 |
| Fatty Compound | DICAPRYLYL CARBONATE, CETYL ALCOHOL, MYRISTIC ACID, PALMITIC ACID, AND/OR STEARIC ACID | 4 |
| Nonionic Emulsifier | GLYCERYL STEARATE (and) PEG-100 STEARATE | 3 |
| Silicone Compound | DIMETHICONE AND/OR DIMETHICONE/VINYL DIMETHICONE CROSSPOLYMER | 3 |
| Filler | SILICA | 3 |
| Water Soluble Solvent | CAPRYLYL GLYCOL AND/OR GLYCERIN | 3 |
| Thickening Agent | AMMONIUM POLYACRYLOYLDIMETHYL TAURATE AND/OR XANTHAN GUM | 1 |
| Miscellaneous | PRESERVATIVE(S), CHELATING AGENT(S), VITAMIN(S), ETC. | ≤3 |
| Carrier | WATER | QS |

Example 3

Comparative Testing

The SPF and UVA-PF for the individual application of Sunscreen Compositions A and B (of Example 2) and for individual application of Skin Perfecting Composition A (of Example 1) were determined. The SPF and UVA-PF for mixtures of Sunscreen Compositions A or B with Skin Perfecting Composition A were also determined. Finally, the SPF and UVA-PF for layered application of Sunscreen Compositions A or B with Skin Perfecting Composition A were determined.

The protocol for determining SPF and UVA-PF was similar to the protocol outlined in L. Fageon et I., International Journal of Cosmetic Science, 2009, Vol. 31, Issue 6, pp. 405-417. The sunscreen compositions were applied in an amount of about 30 mg to a 5 cm×5 cm PMMA plate. The skin perfecting composition was applied in an amount of 60 mg to a 5 cm×5 cm PMMA plate.

Mixtures of the sunscreen compositions and the skin perfecting composition were prepared by mixing the two compositions together in a 2:1 ratio (sunscreen composition: skin perfecting composition). The mixture was applied in an amount of 90 mg to a 5 cm×5 cm PMMA plate.

The sunscreen compositions and the skin perfecting composition were layered onto PMMA plates in the same manner as individually applied (already described), but a drying period of about 15-20 minutes was included between applications. The results are presented in the table below as mean values of three trials for each experiment. The percentages in parenthesis indicate the boost in SPF and UVA-PF relative the individual application of the sunscreen compositions.

| | Treatment | In Vitro SPF | In Vitro UVA-PF |
|---|---|---|---|
| Comparative | Sunscreen A | 13.3 | 7.5 |
| | Sunscreen B | 25.1 | 7.7 |
| | Skin Perfecting Composition A | 0.8 | 0.8 |
| | 2:1 Mixture of Sunscreen A and Skin Perfecting Composition A | 33.6 (+152%) | 15 (+99%) |
| | 2:1 mixture of Sunscreen B and Skin Perfecting Composition A | 27.1 (+8%) | 8.6 (+12%) |
| Inventive | Layered application of Sunscreen A followed by Skin Perfecting Composition A (1:2) | 112.6 (+746%) | 38.1 (+381%) |
| | Layered application of Sunscreen B followed by Skin Perfecting Composition A (1:2) | 235.8 (+839%) | 33.2 (+331%) |
| | Layered application of Skin Perfecting Composition A followed by Sunscreen A (2:1) | 127.5 (+858%) | 39.4 (+425%) |
| | Layered application of Skin Perfecting Composition A followed by Sunscreen B (2:1) | 344.2 (+1271%) | 49.8 (+546%) |

The results show that individual application of the skin perfecting composition provided insignificant SPF and UVA-PF. Mixing the skin perfecting composition with a sunscreen composition improved the SPF and the UVA-PF, but not nearly as much as the improvement in SPF and UVA-PF resulting from layered application of a sunscreen composition and the skin perfecting composition. The degree of improvement for both SPF and UVA-PF resulting from layered application of a sunscreen composition and the skin perfecting composition is surprising and was unexpected.

The foregoing description illustrates and describes the disclosure. Additionally, the disclosure shows and describes only the preferred embodiments and is capable of changes or modifications within the scope of the inventive concepts expressed herein, commensurate with the above teachings and/or the skill or knowledge of the relevant art. The embodiments described herein are intended to explain best modes and to enable others skilled in the art to utilize the disclosure in such, or other, embodiments and variations. Accordingly, the description is not intended to limit the invention. Also, it is intended that the appended claims are construed to include alternative embodiments.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

Some of the various categories of components identified may overlap. In such cases where overlap may exist and the composition includes both components (or the composition includes more than two components that overlap), an overlapping compound does not represent more than one component. For example, a fatty acid may be considered both an emulsifier and a fatty compound. If a particular composition includes both an emulsifier and a fatty compound, a single fatty acid will serve as only the emulsifier or only the fatty compound (the single fatty acid does not serve as both the emulsifier and the fatty component).

The salts referred to throughout the disclosure may include salts having a counter-ion such as an alkali metal, alkaline earth metal, or ammonium counter-ion. This list of counter-ions, however, is non-limiting.

The term "treat" (and its grammatical variations) as used herein refers to the application of the compositions of the present disclosure onto the surface of keratinous substrates such as skin, in particular, the skin of the head, face, and neck.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for perfecting and protecting skin comprising layered application of a skin perfecting composition and a sunscreen composition to the skin,
   (a) the skin perfecting composition comprising:
      (i) about 1 to about 40 wt. %, based on the total weight of the skin perfecting composition, of at least one primary film forming polymer having a Young's modulus of 0.1 to 50 MPa, and elongation at break >50% and a glass transition temperature of <0° C.;
      (ii) about 1 to about 35 wt. %, based on the total weight of the skin perfecting composition, of at least one pressure sensitive adhesive polymer;
      (iii) about 1 to about 35 wt. %, based on the total weight of the skin perfecting composition, of soft focus powder; and
      (iv) water; and
   (b) the sunscreen composition comprising:
      (i) at least one organic UV filter; and
      (ii) a cosmetically acceptable carrier.

2. The method of claim 1 comprising application of the skin perfecting composition to the skin, followed by application of the sunscreen composition onto the skin perfecting composition.

3. The method of claim 1 comprising application of the sunscreen composition to the skin, followed by application of the skin protecting composition onto the sunscreen composition.

4. The method of claim 1, wherein the at least one primary film forming polymer in the skin perfecting composition is a polyurethane latex polymer.

5. The method of claim 4, wherein the at least one polyurethane latex polymer is selected from polycarbonate polyurethane, aliphatic polyurethane, aliphatic polyester polyurethane, Polyurethane 32, polyurethane-34, polyurethane-35, polyurethane-48, and mixtures thereof.

6. The method of claim 5 comprising polyurethane-34, polyurethane-35, or a mixture thereof.

7. The method of claim 1, wherein the total amount of all film forming polymers in the skin perfecting composition is at least 10 wt. %, based on the total weight of the skin perfecting composition.

8. The method of claim 1, wherein the pressure sensitive adhesive polymer in the skin perfecting composition is a pressure sensitive adhesive acrylate polymer.

9. The method of claim 8, wherein the pressure sensitive adhesive acrylate polymer is a copolymer of butyl acrylate, butyl methacrylate, or acrylic acid.

10. The method of claim 9, wherein the pressure sensitive adhesive acrylate polymer is a polymer of 2-ethylhexylacrylate.

11. The method of claim 1, wherein the soft focus powders in the skin perfecting composition are selected from talc, mica, titanated mica, alumina, aluminum silicate, silica which may or may not be coated, fumed silica, silica silylate, polyamide, poly(methyl(meth)acrylate), polyethylene powder, polymethylsilsesquioxane powder, and a mixture thereof.

12. The method of claim 11, wherein the soft focus powders are selected from silica, which may optionally be coated, polymethylsilsesquioxane powder, and a mixture thereof.

13. The method of claim 1, wherein the total amount of soft focus powders in the skin perfecting composition is at least 5 wt. %, based on the total weight of the skin perfecting composition.

14. The method of claim 1, wherein the ratio of the total amount of all film forming polymers to the total amount of soft focus powders in the skin perfecting composition is from about 1:1 to about 6:1.

15. The method of claim 1, wherein the skin perfecting composition comprises:
   (a) about 10 to about 40 wt. %, based on the total weight of the skin perfecting composition, of at least one primary film forming polymer selected from polycarbonate polyurethane, aliphatic polyurethane, aliphatic polyester polyurethane, Polyurethane 32, polyurethane-34, polyurethane-35, polyurethane-48, and mixtures thereof;

(b) about 1 to about 35 wt. %, based on the total weight of the skin perfecting composition, of at least one pressure sensitive adhesive acrylate polymer;

(c) about 1 to about 35 wt. %, based on the total weight of the skin perfecting composition, of soft focus powder selected from talc, mica, titanated mica, alumina, aluminum silicate, silica which may or may not be coated, fumed silica, silica silylate, polyamide, poly(methyl(meth)acrylate), polyethylene powder, polymethylsilsesquioxane powder, and a mixture thereof; and (d) about 25 to about 75 wt. %, based on the total weight of the skin perfecting composition, of water.

16. The method of claim 1, wherein the at least one organic UV filter in the sunscreen composition is selected from a para-aminobenzoate derivative, a salicylate derivative, a cinnamate derivative, a benzophenone or an aminobenzophenone, an anthranillate derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and a mixture thereof.

17. The method of claim 1, wherein the sunscreen composition comprises at least two organic UV filters.

18. The method of claim 17, wherein the sunscreen composition comprises at least one UVA filter and at least one UVB filter.

19. The method of claim 1, wherein the total amount of organic UV filter(s) in the sunscreen composition is from about 1 to about 40 wt. %, based on the total weight of the sunscreen composition.

20. The method of claim 1, wherein the cosmetically acceptable carrier in the sunscreen composition comprises water.

21. The method of claim 1, wherein the sunscreen composition comprises from about 30 to about 90 wt. % of the cosmetically acceptable carrier, based on the total weight of the sunscreen composition.

22. The method of claim 1, wherein the layered application of the skin perfecting composition and the sunscreen composition increases in vitro SPF more than the in vitro SPF obtained by applying a mixture of the skin perfecting composition and the sunscreen composition in the same ratio as the layered application of the skin perfecting composition and the sunscreen composition.

23. The method of claim 1, wherein the layered application of the skin perfecting composition and the sunscreen composition increases in vitro UVA-PF more than the in vitro UVA-PF obtained by applying a mixture of the skin perfecting composition and the sunscreen composition in the same ratio as the layered application of the skin perfecting composition and the sunscreen composition.

* * * * *